United States Patent [19]

Szántay et al.

[11] Patent Number: 4,551,462
[45] Date of Patent: Nov. 5, 1985

[54] EBURNANE DERIVATIVES, PROCESS FOR THEIR PREPARATION AND PHARMACEUTICAL COMPOSITIONS CONTAINING THEM

[75] Inventors: Csaba Szántay; Lajos Szabó; György Kalaus; János Sápi; Éva Pálosi; Béla Kiss; Elemér Ezer; György Hajós, all of Budapest, Hungary

[73] Assignee: Richter Gedeon Vegyeszeti Gyar Rt., Budapest, Hungary

[21] Appl. No.: 508,438

[22] Filed: Jun. 27, 1983

[30] Foreign Application Priority Data

Jun. 30, 1982 [HU] Hungary .............................. 2132/82

[51] Int. Cl.⁴ ................... A61K 31/435; C07D 461/00
[52] U.S. Cl. ....................................... 514/283; 546/51
[58] Field of Search ........................ 546/51; 424/256; 514/283

[56] References Cited

U.S. PATENT DOCUMENTS

| | | | |
|---|---|---|---|
| 3,755,335 | 8/1973 | Thal et al. | 546/51 |
| 3,888,865 | 6/1975 | Szantay et al. | 546/51 |
| 3,937,709 | 2/1976 | Sevenet et al. | 546/51 |
| 4,033,969 | 7/1977 | Sevenét et al. | 546/51 |
| 4,316,028 | 2/1982 | Katsube et al. | 546/51 |

FOREIGN PATENT DOCUMENTS

| | | | |
|---|---|---|---|
| 0765006 | 9/1971 | Belgium | 546/51 |
| 2085630 | 12/1971 | France | 424/256 |
| 2454808 | 12/1980 | France | 424/256 |

*Primary Examiner*—Donald G. Daus
*Assistant Examiner*—Diana G. Rivers
*Attorney, Agent, or Firm*—Karl F. Ross; Herbert Dubno

[57] ABSTRACT

The invention relates to racemic or optically active eburnane derivatives of the formula (I),

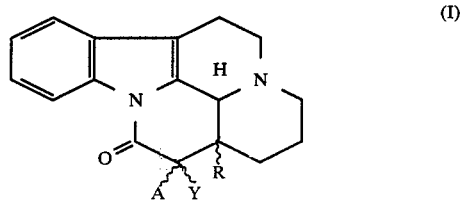

wherein
R represents an alkyl group having 1 to 6 carbon atoms,
A stands for hydroxyl and
Y is hydrogen, or
A and Y together form an oxo group,
and the configuration of the hydrogen in the 3-position and of R is α,α and/or β,β or α,β and/or β,α,
and acid addition salts thereof.

The new compounds possess valuable pharmaceutical properties, thus their certain representatives show antiallergic activity, while others are potent antidepressive, gastric secretion inhibiting and anticonvulsive agents. The compounds of the formula (I) and pharmaceutically acceptable acid addition salts thereof can therefore be employed as active ingredients of pharmaceutical compositions, which are also within the scope of the invention.

7 Claims, No Drawings

EBURNANE DERIVATIVES, PROCESS FOR THEIR PREPARATION AND PHARMACEUTICAL COMPOSITIONS CONTAINING THEM

The invention relates to new eburnane derivatives, process for their preparation and pharmaceutical compositions containing them as active ingredient. More particularly, the invention concerns new racemic and optically active eburnane derivatives of the formula (I),

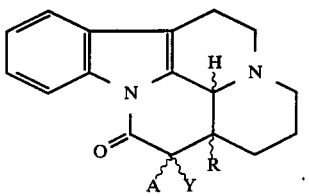

wherein
R represents an alkyl group having 1 to 6 carbon atoms,
A stands for hydroxyl and
Y is hydrogen, or
A and Y together form an oxo group,
and the configuration of the hydrogen in the 3-position and of R is α,α and/or β,β or α,β and/or β,α and acid addition salts thereof.

According to another aspect of the invention there is provided a process for the preparation of the racemic or optically active eburnane derivatives of the formula (I), in which R, A,Y and the configuration of the 3-hydrogen and R are as defined above by desoximating a racemic or optically active eburnane-oxime derivative of the formulae (IIa) and/or (IIb)

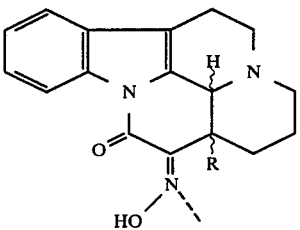

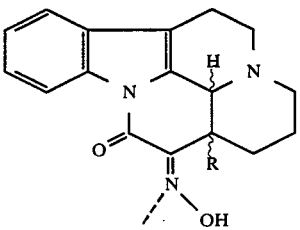

in which R and the configuration of the 3-hydrogen and R are as defined above, or an acid addition salt thereof and, if desired, treating the product obtained with an acid and/or, if desired, partially reducing a racemic or optically active eburnane derivative of the formula (I) obtained, in which A and Y together form an oxo group, and R and the configuration of the 3-hydrogen and R are the same as defined above, or acid addition salts thereof and, if desired, separating an eburnane derivative of the formula (I), in which A is hydroxyl, Y is hydrogen and the configuration of the 3-hydrogen and R is as defined above, obtained as a 15-epimeric mixture into the corresponding epimers, or converting a 15-epimer into another 15-epimer and/or, if desired, resolving a racemic eburnane derivative of the formula (I) obtained and/or, if desired, treating a racemic or optically active eburnane derivative of the formula (I) or a 15-epimer thereof with an acid.

In the above formulae R is an alkyl group having 1 to 6 carbon atoms may represent a straight or branched chained alkyl group such as methyl, ethyl, n-propyl, i-propyl, n-butyl, sec-butyl, tert-butyl, n-pentyl, i-pentyl, n-hexyl or i-hexyl group.

The new racemic or optically active starting compounds of the formulae (IIa) and/or (IIb) are prepared from the corresponding eburnamonine derivatives by oximation, preferably with a tertiary $C_{4-8}$-alkyl nitrite, in the presence of a strong base.

The desoximation of the compounds of the formulae (IIa) and/or (IIb) can be carried out hydrolytically, for example with a dilute aqueous hydrochloric acid solution and formaldehyde or levulic acid, or with a mixture of pyroracemic acid and a mineral acid, or with an aqueous solution of sodium hydrogensulfite; or in an oxidative route, for example with cerium(IV)-ammonium nitrate, lead(IV) acetate, thallium(III) nitrate, periodic acid, with a mixture of chromium trioxide and sulfuric acid or acetic acid, ozone or with a mixture of palladium, triphenyl phosphite and oxygen; or by a reductive process, for instance with titanium-(III) chloride, chromium(II) acetate, Raney nickel in an alkaline medium or with zinc in an acetic acid medium, or with acetone by transoximation.

In the process according to the invention desoximation is preferably carried out hydrolytically. More preferably, the new racemic or optically active compounds of the formulae (IIa) and/or (IIb) are heated with an aqueous solution of a mineral acid, e.g. hydrochloric acid or sulfuric acid, at a temperature between 60° C. and 120° C., preferably 95° C. to 105° C.

When monitoring the desoximation by thin layer chromatography it has been found that if a Z-isomer of the formula (IIa) is used as a starting material, it is converted first into the corresponding E-isomer of the formula (IIb), which is more stable thermodynamically, i.e. as a first step a transisomerization takes place, consequently, the desoximation is always performed on the oxime derivatives of the formula (IIb).

The partial reduction of the compounds of the formula (I), in which A and Y together form an oxo group, can be accomplished by any method known in the art which is suitable for the reduction of the 15-oxo group into an alcoholic hydroxyl group, while leaving the 14-oxo group unchanged. We have found that for example alkali metal borohydrides, such as sodium borohydride or sodium cyanoborohydride are suitable for this purpose. The partial reduction is preferably carried out in an organic solvent, being inert under the reduction conditions, preferably in an alkanol having 1 to 6 carbon atoms, such as methanol, or in a mixture of an alkanol having 1 to 6 carbon atoms and a halogenated aliphatic hydrocarbon. The temperature of the partial reduction is preferably low, most preferably between 0° C. and 5° C.

If compounds of the formula (I), in which A stands for hydroxyl and Y is hydrogen, are prepared by the process according to the invention, these groups have an $\alpha,\beta$ and/or $\beta,\alpha$ configuration. If an epimeric mixture is obtained, this can be separated into the corresponding epimers by known techniques, for example by column or thin layer chromatography. If the reaction affords a 15-epimer, this can be converted into the other 15-epimer in a known manner.

In the starting compounds of the formulae (IIa) and/or (IIb) the mutual configuration of the hydrogen in the 3-position and the R substituent is not changed during the process according to the invention, accordingly, in the end products of the formula (I) the configuration of the 3-hydrogen and R is the same as in the starting compounds of the formulae (IIa) and/or (IIb).

If desired, the compounds of the formula (I) may be converted into their acid addition salts. Suitable acids for this purpose are inorganic acids, such as hydrogen halides (e.g. hydrochloric acid, hydrogen bromide), sulfuric acid, phosphoric acid, nitric acid, perhaloic acids (e.g. perchloric acid), etc.; organic carboxylic acids, such as formic acid, acetic acid, propionic acid, glycolic acid, maleic acid, hydroxymaleic acid, fumaric acid, succinic acid, tartaric acid, ascorbic acid, citric acid, malic acid, salicylic acid, lactic acid, cinnamic acid, benzoic acid, phenylacetic acid, p-aminobenzoic acid, p-hydroxybenzoic acid, p-aminosalicylic acid, etc.; alkylsulfonic acids, such as methanesulfonic acid, ethanesulfonic acid, etc.; cycloaliphatic acids, e.g. cyclohexylsulfonic acid; arylsulfonic acids, e.g. p-toluenesulfonic acid, naphthylsulfonic acid, sulfamilic acid, etc.; amino acids, such as asparaginic acid, glutamic acid, N-acetyl-asparaginic acid, N-acetyl-glutaric acid, etc.

The salts are generally prepared in an inert organic solvent, for example in an aliphatic alcohol having 1 to 6 carbon atoms, by dissolving the racemic or optically active compound of the formula (I) in said solvent, adding the corresponding acid into the solution while the pH of the mixture becomes slightly acidic (pH 5-6) and subsequently separating the precipitated acid addition salt from the reaction mixture by a suitable method, e.g. by filtration.

The racemic compounds of the formula (I) can be resolved by known techniques but optically active end-products may also be prepared by starting from the corresponding optically active starting compounds of the formulae (IIa) and/or (IIb). Preferably, racemic products of the formula (I) are prepared directly from the corresponding racemic starting compounds of the formulae (IIa) and/or (IIb), while the optically active compounds of the formula (I) are preferably obtained by starting from the corresponding optically active compounds of the formulae (IIa) and/or (IIb).

If desired, the racemic or optically active compounds of the formula (I) or acid addition salts thereof may be subjected to further purification, e.g. recrystallization. The solvents used for recrystallization are selected in accordance with the solubility and the crystallizability of the compounds to be recrystallized.

The compounds of the formula (I) possess valuable pharmaceutical activities, namely antiallergic activity, and are potent antidepressive, gastric secretion inhibiting and anticonvulsive agents.

According to another aspect of the invention there are provided pharmaceutical compositions containing at least one compound of the formula (I) or a pharmaceutically acceptable salt thereof as an active ingredient.

The active ingredients of the formula (I) or pharmaceutically acceptable acid addition salts thereof can be converted into pharmaceutical compositions for parenteral or enteral administration by admixing them with solid and/or liquid carriers and/or further additives conventionally used in the preparation of pharmaceutical compositions. As a carrier for example water, gelatine, lactose, starch, pectine, magnesium stearate, stearic acid, talc, vegetable oils (e.g. peanut oil, olive oil), etc. can be employed.

The compositions may be finished in the form of solid (e.g. tablets, lozenges, dragees, capsules, such as hard gelatine capsules, suppositories, etc.) or liquid (.e.g oily or aqueous solutions, suspensions, emulsions, syrups, soft gelatine capsules, injectable oily or aqueous solutions or suspensions, etc.) formulations. The quantity of the solid carrier can be varied within a wide range but preferably is about between 25 mg. and 1 g. per dosage unit. The pharmaceutical compositions optionally contain also conventional pharmaceutical additives, such as preservatives, stabilizing, wetting, emulsifying agents, salts capable of adjusting the osmotic pressure, buffers, flavoring agents, aroma agents, etc. Optionally further pharmaceutically active compounds can also be present in the formulations.

The pharmaceutical compositions are preferably manufactured in dosage units containing 10 micrograms to 100 mg. of the active agent, suitable for the desired route of administration. The pharmaceutical compositions may be prepared by conventional techniques which comprise for example screening, admixing, granulating, pressing or dissolving the components. The compositions obtained can be subjected to further operations conventionally used in the pharmaceutical industry, for example sterilization.

Further details of the present invention are to be found in the following Examples which are, however, by no means intended to limit the scope of the protection sought.

EXAMPLE 1

($-$)-14,15-Dioxo-eburnane($3\alpha,16\alpha$)

2.0 g. (6.2 mmoles) of ($+$)-14-oxo-15-hydroxyimino-eburnane($3\alpha,16\alpha$) are heated with 12 ml. of a 15% aqueous hydrochloric acid solution on water bath for 1 to 1.5 hours. The reaction mixture is allowed to cool down and the pH is adjusted to 9 with a concentrated aqueous ammonium hydroxide solution under cooling with ice. The precipitated substance is extracted with three 30-ml. portions of dichloromethane, the organic phases are combined, dried with solid, anhydrous magnesium sulfate, filtered and from the filtrate the solvent is eliminated by distillation in vacuo. The residual oil is crystallized from 4 ml. of ethanol. 1.50 g. of the title compound are obtained.

Yield: 78.5%

According to thin layer chromatography the $R_f$-value of the end-product is higher than that of the starting material (KG-G, benzene:methanol=14:3).

Melting point: 161° to 162° C. (ethanol)

Analysis for $C_{19}H_{20}N_2O_2$ (308.38): calculated: C 74.00%, H 6.54%, N 9.08%; found: C 74.32%, H 6.68%, N 9.29%.

IR spectrum (KBr): 1735, 1720 $cm^{-1}$ (CO)

Mass spectrum (m/e, %): 309 (M+1, 24), 308 (M+, 100), 307 (66), 279 (22), 252 (70).

$^1$H-NMR spectrum (CDCl$_3$, δ): 8.50–7.25 (4H,m, aromatic), 4.39 (1H, s, 3-H), 1.03 (3H, t, J=7 Hz, CH$_2$CH$_3$).

$^{13}$C-NMR (CDCl$_3$, δ): 194.2 (CO-15), 153.3 (CO-14), 134.0 (C-13), 130.2 (C-2), 129.7 (C-8), 125.3 (C-10), 125.1 (C-11), 118.5 (C-9), 116.7 (C-12), 115.2 (C-7), 52.9 (C-3), 52.2 (C-16), 50.7 (C-5), 44.26 (C-19), 27.3 (C-17), 23.2 (C-20), 20.3 (C-18), 16.5 (C-6), 9.1 (C-21).

EXAMPLE 2

(−)-14-Oxo-15α-hydroxy-eburnane(3α,16α)

4.00 g. (13 mmoles) of (−)-14,15-dioxo-eburnane prepared according to Example 1 are dissolved in 40 ml. of absolute methanol under heating, whereupon 240 mg. (6.5 mmoles) of sodium borohydride are added to the solution portionwise, under cooling with ice, at 0° C.

The reaction is monitored by thin layer chromatography. The R$_f$-value of the starting compound is higher than that of the end product (KG-G, dichloromethane:methanol=20:1).

After termination of the reduction the excess of the reducing agent is decomposed with glacial acetic acid under cooling with ice, whereupon the solvent is eliminated by distillation in vacuo. The residue is dissolved in 15 ml. of dichloromethane and is extracted after adjusting the pH to alkaline by adding 10 ml. of a 10% aqueous sodium carbonate solution. The separated aqueous phase is shaken with two 10-ml. portions of dichloromethane, the organic phases are combined, dried over solid, anhydrous magnesium sulfate, filtered and from the filtrate the solvent is eliminated by distillation in vacuo. 4.6 g. of an oily product are obtained, which are dissolved in 8 ml. of methanol and the pH of the solution is adjusted to 2 with hydrochloric acid in methanol.

3.83 g. of the title compound are obtained in a crystalline form, as a hydrochloride salt.

Yield: 85.5%

Melting point: 255° C. (decomp.)

$[\alpha]_D^{26} = -67°$; $[\alpha]_{546}^{26} = -78°$ (salt, c=1, dimethylformamide).

IR spectrum (KBr): 3380 (OH), 1722 cm$^{-1}$ (CO)

Mass spectrum (m/e, %): 311 (M+1, 22), 310 (M+, 100), 309 (65), 281 (3,4), 263 (4,1), 253 (21), 240 (3,3), 224 (4), 212 (3,2), 168 (3), 167 (2,8).

$^1$H-NMR spectrum (CDCl$_3$, δ): 8.35–7.25 (4H, m, aromatic), 4.38 (1H, s, 15-H), 4.06 (1H, s, 3-H), 3.48 (1H, s, OH), 1.07 (3H, t, J=5 Hz, CH$_2$CHHD 3).

$^{13}$C-NMR (CDCl$_3$, δ): 170.52 (C-14), 133.94 (C-13), 131.41 (C-2), 130.40 (C-8), 124.44–124.21 (C-11, C-10), 118.24 (C-9), 115.94 (C-12), 113.42 (C-7), 73.87 (C-15), 53,74 (C-3), 50.50 (C-5), 44.76 (C-19), 43.49 (C-16), 25.05–24.82 (C-17, C-20), 20.19 (C-18), 1672 (C-6), 8.35 (C-21).

We claim:

1. A compound of the Formula (I)

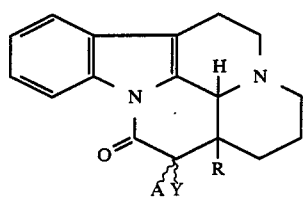

(I)

wherein

R is ethyl,

A is hydroxyl, and

Y is hydrogen, or

A and Y together form an oxo group, or a pharmaceutically acceptable acid addition salt thereof.

2. (−)-14,15-dioxo-eburnane(3alpha,16alpha) or a pharmaceutically acceptable acid addition salt thereof.

3. (−)-14-oxo-15-alpha-hydroxy-eburnane(3alpha,16alpha) or a pharmaceutically acceptable acid addition salt thereof.

4. An antidepressant pharmaceutical composition which comprises a pharmaceutically effective amount of the compound defined in claim 2 or a pharmaceutically acceptable acid addition salt thereof.

5. An anticonvulsive pharmaceutical composition which comprises a pharmaceutically effective amount of the compound defined in claim 3 or a pharmaceutically acceptable acid addition salt thereof.

6. An antidepressant method of treatment which comprises the step of administering to a subject in need of said treatment a pharmaceutically effective amount of the compound of the Formula (I) defined in claim 1 or a pharmaceutically acceptable acid addition salt thereof.

7. An anticonvulsive method of treatment which comprises the step of administering to a subject in need of said treatment a pharmaceutically effective amount of the compound of the Formula (I) defined in claim 1 or a pharmaceutically acceptable acid addition salt thereof.

* * * * *